US011202783B2

(12) United States Patent
Jun et al.

(10) Patent No.: US 11,202,783 B2
(45) Date of Patent: *Dec. 21, 2021

(54) USE OF AMINOALKYLBENZOTHIAZEPINE DERIVATIVES

(71) Applicant: CJ Healthcare Corporation, Seoul (KR)

(72) Inventors: Hyungjin Jun, Gyeonggi-do (KR); So Young Ki, Gyeonggi-do (KR); Keunho Lee, Seoul (KR); Jin Woo Jung, Seoul (KR); Dong Hyun Kim, Gyeonggi-do (KR); Chi Hye Park, Gyeonggi-do (KR); Hyoung Rok Bak, Seoul (KR); Shin-Young Ryu, Gyeonggi-do (KR); Ju Hyun Lee, Gyeonggi-do (KR); Ho-Youl Lee, Gyeonggi-do (KR); Won-Hyuk Jung, Gyeonggi-do (KR); Dong Hyun Ko, Gyeonggi-do (KR); Seungin Kim, Gyeonggi-do (KR); Joonseok Byun, Gyeonggi-do (KR); Jae Ho Yoo, Gyeonggi-do (KR); Seunghee Ji, Seoul (KR)

(73) Assignee: CJ Healthcare Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/631,611

(22) PCT Filed: Jul. 20, 2018

(86) PCT No.: PCT/KR2018/008211
§ 371 (c)(1),
(2) Date: Jan. 16, 2020

(87) PCT Pub. No.: WO2019/017724
PCT Pub. Date: Jan. 24, 2019

(65) Prior Publication Data
US 2020/0147101 A1  May 14, 2020

(30) Foreign Application Priority Data
Jul. 21, 2017 (KR) .......... 10-2017-0092852

(51) Int. Cl.
*A61K 31/554* (2006.01)

(52) U.S. Cl.
CPC .................. *A61K 31/554* (2013.01)

(58) Field of Classification Search
CPC .................................. A61K 31/554
See application file for complete search history.

(56) References Cited

U.S. PATENT DOCUMENTS

| 9,890,129 B2 * | 2/2018 | Jung ............ C07C 13/24 |
| 2003/0153513 A1 | 8/2003 | Shiomi et al. |
| 2004/0254160 A1 | 12/2004 | Starke et al. |
| 2006/0083790 A1 | 4/2006 | Anderberg et al. |

FOREIGN PATENT DOCUMENTS

| EP | 3210977 A2 | 8/2017 |
| JP | H11-500102 A | 1/1999 |
| JP | 2003-525933 A | 9/2003 |
| JP | 2012-224590 A | 11/2012 |
| KR | 10-2016-0047378 A | 5/2016 |
| KR | 10-1844184 B1 | 4/2018 |
| WO | 2016/064082 A2 | 4/2016 |

OTHER PUBLICATIONS

International Search Report issued in corresponding International Patent Application No. PCT/KR2018/008211 dated Nov. 5, 2018.
Written Opinion issued in corresponding International Patent Application No. PCT/KR2018/008211 dated Nov. 5, 2018.
Okudaira et al., "Contribution of intestinal transporters to drug absorption and the implications for drug discovery and development (1)-influx transporters," Drug Delivery System, 21-2: 134-141 (2006) (see English abstract).
Dawson et al., "Role of the Intestinal Bile Acid Transporters in Bile Acid and Drug Disposition," Handbook of Experimental Pharmacology, 201: 169-203 (2011).
Siebers et al., "Absorption, Distribution, Metabolism, and Excretion of [14C]-Volixibat in Healthy Men: Phase 1 Open-Label Study," European Journal of Drug Metabolism and Pharmacokinetics, 43 (1): 91-101 (2018).
Extended European Search Report issued in related European Patent Application No. 18835549.9 dated March 26, 2021.

* cited by examiner

*Primary Examiner* — Brenda L Coleman
(74) *Attorney, Agent, or Firm* — Morgan, Lewis & Bockius LLP

(57) ABSTRACT

The present disclosure relates to a pharmaceutical composition for preventing or treating non-alcoholic fatty liver disease or dyslipidemia comprising an aminoalkylbenzothiazepine derivative or a pharmaceutically acceptable salt thereof as an active ingredient.

18 Claims, 4 Drawing Sheets

USE OF AMINOALKYLBENZOTHIAZEPINE DERIVATIVES

TECHNICAL FIELD

The present disclosure relates to a pharmaceutical composition for preventing or treating non-alcoholic fatty liver disease or dyslipidemia comprising an aminoalkylbenzothiazepine derivative or a pharmaceutically acceptable salt thereof as an active ingredient.

BACKGROUND ART

Fatty liver is defined as a case in which the weight due to fat deposition in the liver exceeds 5% of liver weight. Non-alcoholic fatty liver disease (hereinafter, NAFLD) specifically refers to a case in which fatty liver is not caused by viruses, drugs, heredity, or alcohol. NAFLD, which is a chronic liver disease known to be closely related to metabolic syndrome (e.g., insulin resistance, obesity, hypertension, dyslipidemia, etc.), includes a whole series of processes that result in diseases ranging from simple steatosis in the liver to non-alcoholic steatohepatitis and cirrhosis. Reportedly, the prevalence of NAFLD varies from population to population globally; for example, in the western world, NAFLD is known to occur in about 20% to 30% of normal adults without any particular cause of liver disease, whereas the prevalence of NAFLD is about 16% to 50% of adults in Korea. In general, NAFLD is known to have increased prevalence in those having obesity, and this is reportedly because insulin resistance in obesity is an important cause of fat deposition in the liver. Simple steatosis (e.g., simple fat deposition), which is a mild fatty liver without any damage to the liver cells, has a relatively good prognosis. If left untreated, however, it can progress to cirrhosis, a serious liver disease. It is known that 4% to 27% of cirrhosis patients may develop liver cancer, and that 30% to 40% of cirrhosis patients may die within 10 years due to complications of liver disease and cardiovascular disease. Therefore, NAFLD is a disease that requires active management from the early stages of the disease.

NAFLD has been treated using pioglitazone, vitamin E, ursodeoxycholic acid (UDCA), etc. However, the effects of these drugs remain insufficient and may cause side effects when administered for a long period of time. Therefore, no drug has been approved for the treatment of NAFLD until now.

DISCLOSURE

Technical Problem

The present inventors have made efforts to develop a small molecular compound capable of preventing or treating non-alcoholic fatty liver disease (NAFLD) or dyslipidemia. As a result, they have discovered that some aminoalkylbenzothiazepine derivatives exhibit the effects of reducing fat accumulation in the liver, inhibiting liver fibrosis, and controlling lipid levels in the blood, thereby completing the present disclosure.

Technical Solution

An object of the present disclosure is to provide a pharmaceutical composition for preventing or treating NAFLD or dyslipidemia comprising an aminoalkylbenzothiazepine derivative or a pharmaceutically acceptable salt thereof as an active ingredient.

Another object of the present disclosure is to provide a method for preventing or treating NAFLD or dyslipidemia, which includes administering the pharmaceutical composition to a subject in need thereof.

Advantageous Effects

The aminoalkylbenzothiazepine derivatives of the present disclosure not only have the effect of preventing fat accumulation in the liver by inhibiting fat synthesis and fibrosis, but also have the effect of controlling blood cholesterol levels. This suggests that the compounds of the present disclosure can be effectively used for the prevention and treatment of dyslipidemia as well as non-alcoholic fatty liver disease (NAFLD).

BEST MODE

To achieve the above objects, in an aspect of the present disclosure, there is provided a pharmaceutical composition for preventing or treating NAFLD or dyslipidemia comprising an aminoalkylbenzothiazepine derivative or a pharmaceutically acceptable salt thereof as an active ingredient.

In another aspect of the present disclosure, there is provided a method for preventing or treating NAFLD or dyslipidemia which includes administering the pharmaceutical composition to a subject in need thereof.

Hereinafter, the present disclosure will be described in more detail.

The present inventors previously synthesized a series of novel aminoalkylbenzothiazepine derivatives through previous studies and confirmed that these compounds were effective for the prevention and treatment of constipation (KR Patent No. 10-1674806). However, the effects of these compounds on NAFLD have not been confirmed.

The present disclosure is based on the discovery that these aminoalkylbenzothiazepine derivatives exhibit effects of preventing or treating dyslipidemia as well as NAFLD.

The aminoalkylbenzothiazepine derivatives of the present disclosure may be a compound represented by Formula 1 below:

[Formula 1]

In Formula 1 above, $R_1$ may be hydroxy, carboxy, or hydroxysulfonyl($C_{1-4}$ alkyl); $R_2$ and $R_3$ may each independently be hydrogen, $C_{1-4}$ alkyl, hydroxy($C_{1-4}$ alkyl), carbamoyl($C_{1-4}$ alkyl), carboxy, carboxy($C_{1-4}$ alkyl), ($C_{5-10}$ heteroaryl)($C_{1-4}$ alkyl) or ($C_{5-10}$ aryl)($C_{1-4}$ alkyl), or $R_2$ and $R_3$, taken together with the respective carbon atom to which they are attached, may form $C_{3-7}$ cycloalkyl; $R_4$ may be hydrogen or carboxy($C_{1-4}$ alkyl); $R_5$ may be hydrogen, halogen, ($C_{1-4}$ alkyl)thio, ($C_{1-4}$ alkyl)amino, or di($C_{1-4}$ alkyl)amino; $R_6$ and $R_7$ may each independently be $C_{1-6}$ alkyl; $R_8$ and $R_9$ may each independently be hydrogen, hydroxy, $C_{1-4}$ alkoxy, $C_{1-4}$ alkyl, halogen, nitro, cyano, amino, ($C_{1-4}$ alkyl)amino, di($C_{1-4}$ alkyl)amino, acetamido, formyl, $C_{1-4}$ alkanoyl, carboxy, carbamoyl, ($C_{1-4}$ alkyl)carbamoyl, di($C_{1-4}$ alkyl)carbamoyl, carbamoyloxy, ($C_{1-4}$ alkyl)carbamoyloxy, di($C_{1-4}$ alkyl)carbamoyloxy, ($C_{1-4}$ alkyl)sulfonyloxy, sulfamoyloxy, ($C_{1-4}$ alkyl)sulfamoyloxy, or di($C_{1-4}$ alkyl)sulfamoyloxy; Q may be $C_{5-10}$ aryl or $C_{5-10}$ heteroaryl; and n may be an integer of 0 to 3.

For example, in Formula 1 above, $R_1$ may be hydroxy, carboxy, or hydroxysulfonyl($C_{1-4}$ alkyl); $R_2$ and $R_3$ may each independently be hydrogen, $C_{1-4}$ alkyl, hydroxy($C_{1-4}$ alkyl), carbamoyl($C_{1-4}$ alkyl), carboxy, carboxy($C_{1-4}$ alkyl), or ($C_{5-10}$ heteroaryl)($C_{1-4}$ alkyl), or $R_2$ and $R_3$, taken together with the respective carbon atom to which they are attached, may form $C_{3-7}$ cycloalkyl; $R_4$ may be hydrogen or carboxy($C_{1-4}$ alkyl); $R_5$ may be ($C_{1-4}$ alkyl)thio, or di($C_{1-4}$ alkyl)amino; $R_6$ and $R_7$ may each independently be $C_{1-6}$ alkyl; $R_8$ and $R_9$ may each independently be hydrogen, hydroxy, halogen, or $C_{1-4}$ alkoxy; Q may be $C_{5-10}$ aryl; and n may be an integer of 0 to 3.

Specifically, in Formula 1 above, $R_1$ may be hydroxy, carboxy, or hydroxysulfonylmethyl.

Specifically, in Formula 1 above, $R_2$ and $R_3$ may each independently be hydrogen, carboxy, methyl, isobutyl, carbamoylmethyl, carboxymethyl, carboxyethyl, hydroxymethyl, imidazolylmethyl, indolylmethyl, or ethyl, or $R_2$ and $R_3$, taken together with the respective carbon atom to which they are attached, may form cyclopropyl.

Specifically, in Formula 1 above, $R_4$ may be hydrogen, carboxymethyl, or carboxyethyl.

Specifically, in Formula 1 above, $R_5$ may be methylthio, ethylthio, or dimethylamino.

Specifically, in Formula 1 above, $R_6$ and $R_7$ may both be butyl or ethyl.

Specifically, in Formula 1 above, $R_8$ and $R_9$ may each independently be hydrogen, hydroxy, methoxy, methyl, ethyl, fluoro, chloro, nitro, cyano, amino, methylamino, ethylamino, dimethylamino, acetyl, carboxy, carbamoyl, methylcarbamoyl, dimethylcarbamoyl, carbamoyloxy, methylcarbamoyloxy, dimethylcarbamoyloxy, methylsulfonyloxy, sulfamoyloxy, methylsulfamoyloxy, or dimethylsulfamoyloxy.

Specifically, in Formula 1 above, Q may be phenyl, pyridinyl, pyrimidinyl, or thiophenyl. According to Formula 1, Q may be phenyl, pyridinyl, pyrimidinyl, or thiophenyl substituted with $R_8$ and $R_9$. In Q above, the positions of $R_8$ and $R_9$ are not determined and may be located on mutually different atoms, and hydrogen may be bound to positions other than these positions. Accordingly, when both $R_8$ and $R_9$ are hydrogen, Q may refer to phenyl, pyridinyl, pyrimidinyl, or thiophenyl, which are not substituted.

More specifically, the compound may be: 2-(((3,3-dibutyl-7-methylthio-1,1-dioxido-5-phenyl-2,3,4,5-tetrahydrobenzo[b][1,4]thiazepin-8-yl)methyl)amino)acetic acid; 3-(((3,3-dibutyl-7-methylthio-1,1-dioxido-5-phenyl-2,3,4,5-tetrahydrobenzo[b][1,4]thiazepin-8-yl)methyl)amino)propanoic acid; 2-(((3,3-dibutyl-7-methylthio-1,1-dioxido-5-phenyl-2,3,4,5-tetrahydrobenzo[b][1,4]thiazepin-8-yl)methyl)amino)succinic acid; (S)-2-(((3,3-dibutyl-7-methylthio-1,1-dioxido-5-phenyl-2,3,4,5-tetrahydrobenzo[b][1,4]thiazepin-8-yl)methyl)amino)propanoic acid; 2-(((3,3-dibutyl-7-methylthio-1,1-dioxido-5-phenyl-2,3,4,5-tetrahydrobenzo[b][1,4]thiazepin-8-yl)methyl)amino)pentanedioic acid; 4-amino-2-(((3,3-dibutyl-7-methylthio-1,1-dioxido-5-phenyl-2,3,4,5-tetrahydrobenzo[b][1,4]thiazepin-8-yl)methyl)amino)-4-oxobutanoic acid; (R)-2-(((3,3-dibutyl-7-methylthio-1,1-dioxido-5-phenyl-2,3,4,5-tetrahydrobenzo[b][1,4]thiazepin-8-yl)methyl)amino)propanoic acid; 2-(((3,3-dibutyl-7-methylthio-1,1-dioxido-5-phenyl-2,3,4,5-tetrahydrobenzo[b][1,4]thiazepin-8-yl)methyl)amino)-2-methylpropanoic acid; (R)-2-(((3,3-dibutyl-7-methylthio-1,1-dioxido-5-phenyl-2,3,4,5-tetrahydrobenzo[b][1,4]thiazepin-8-yl)methyl)amino)-3-(1H-imidazol-4-yl)propanoic acid; (R)-2-(((3,3-dibutyl-7-methylthio-1,1-dioxido-5-phenyl-2,3,4,5-tetrahydrobenzo[b][1,4]thiazepin-8-yl)methyl)amino)-3-(1H-indol-2-yl)propanoic acid; (S)-2-(((3,3-dibutyl-7-methylthio-1,1-dioxido-5-phenyl-2,3,4,5-tetrahydrobenzo[b][1,4]thiazepin-8-yl)methyl)amino)-4-methylpentanoic acid; (S)-2-(((3,3-dibutyl-7-methylthio-1,1-dioxido-5-phenyl-2,3,4,5-tetrahydrobenzo[b][1,4]thiazepin-8-yl)methyl)amino)pentanedioic acid; (S)-2-(((3,3-dibutyl-7-methylthio-1,1-dioxido-5-phenyl-2,3,4,5-tetrahydrobenzo[b][1,4]thiazepin-8-yl)methyl)amino)-3-hydroxypropanoic acid; 3-((carboxymethyl)((3,3-dibutyl-7-methylthio-1,1-dioxido-5-phenyl-2,3,4,5-tetrahydrobenzo[b][1,4]thiazepin-8-yl)methyl)amino)propanoic acid; 3-(((3,3-dibutyl-7-methylthio-1,1-dioxido-5-phenyl-2,3,4,5-tetrahydrobenzo[b][1,4]thiazepin-8-yl)methyl)amino)pentanedioic acid; 2-(((3,3-dibutyl-7-methylthio-1,1-dioxido-5-phenyl-2,3,4,5-tetrahydrobenzo[b][1,4]thiazepin-8-yl)methyl)amino)-2-oxoacetic acid; 1-(((3,3-dibutyl-7-methylthio-1,1-dioxido-5-phenyl-2,3,4,5-tetrahydrobenzo[b][1,4]thiazepin-8-yl)methyl)amino)cyclopropanecarboxylic acid; 2-(((3,3-dibutyl-7-methylthio-1,1-dioxido-5-phenyl-2,3,4,5-tetrahydrobenzo[b][1,4]thiazepin-8-yl)methyl)amino)-2-oxoethanesulfonic acid; 2-(((3,3-dibutyl-5-(4-methoxyphenyl)-7-methylthio-1,1-dioxido-2,3,4,5-tetrahydrobenzo[b][1,4]thiazepin-8-yl)methyl)amino)acetic acid; 2-(((3,3-dibutyl-5-(4-hydroxyphenyl)-7-methylthio-1,1-dioxido-2,3,4,5-tetrahydrobenzo[b][1,4]thiazepin-8-yl)

methyl)amino)acetic acid; 2-(((3,3-dibutyl-5-(3-methoxyphenyl)-7-methylthio-1,1-dioxido-2,3,4,5-tetrahydrobenzo[b][1,4]thiazepin-8-yl)methyl)amino)acetic acid; 2-(((3,3-dibutyl-5-(4-fluorophenyl)-7-methylthio-1,1-dioxido-2,3,4,5-tetrahydrobenzo[b][1,4]thiazepin-8-yl)methyl)amino) acetic acid; 2-(((3,3-dibutyl-5-(3-fluorophenyl)-7-methylthio-1,1-dioxido-2,3,4,5-tetrahydrobenzo[b][1,4]thiazepin-8-yl)methyl)amino)acetic acid; 2-(((3,3-dibutyl-5-(3-fluoro-4-methoxyphenyl)-7-methylthio-1,1-dioxido-2,3,4,5-tetrahydrobenzo[b][1,4]thiazepin-8-yl)methyl)amino) acetic acid; 2-(((3,3-dibutyl-5-(4-methoxyphenyl)-7-methylthio-1,1-dioxido-2,3,4,5-tetrahydrobenzo[b][1,4]thiazepin-8-yl)methyl)amino)-2-oxoethanesulfonic acid; 1-(((3,3-dibutyl-5-(3-fluoro-4-methoxyphenyl)-7-methylthio-1,1-dioxido-2,3,4,5-tetrahydrobenzo[b][1,4]thiazepin-8-yl)methyl)amino)cyclopropanecarboxylic acid; 2-(((3,3-dibutyl-5-(4-fluorophenyl)-7-methylthio-1,1-dioxido-2,3,4,5-tetrahydrobenzo[b][1,4]thiazepin-8-yl)methyl)amino)-2-oxoacetic acid; (S)-2-(((3,3-dibutyl-5-(4-fluorophenyl)-7-methylthio-1,1-dioxido-2,3,4,5-tetrahydrobenzo[b][1,4]thiazepin-8-yl)methyl)amino)propanoic acid; (S)-2-(((3,3-dibutyl-5-(4-fluorophenyl)-7-methylthio-1,1-dioxido-2,3,4,5-tetrahydrobenzo[b][1,4]thiazepin-8-yl)methyl)amino)-3-hydroxypropanoic acid; or 1-(((3,3-dibutyl-5-(4-fluorophenyl)-7-methylthio-1,1-dioxido-2,3,4,5-tetrahydrobenzo[b][1,4]thiazepin-8-yl)methyl)amino) cyclopropanecarboxylic acid.

Additionally, the compounds of the present disclosure may be present in the form of a pharmaceutically acceptable salt. As the salt, an acid addition salt formed by a pharmaceutically acceptable free acid is useful. As used herein, the term "pharmaceutically acceptable salt" refers to any organic or inorganic acid addition salt of the compound, which has a concentration that is relatively non-toxic and harmless to patients, and the side effects caused by this salt do not deteriorate the beneficial effects of the compounds represented by Formula 1.

Acid addition salts can be prepared by a conventional method, for example, by dissolving the compound in an excess amount of an aqueous acid solution and precipitating the salt using a water-miscible organic solvent (e.g., methanol, ethanol, acetone, acetonitrile, etc.). An equimolar amount of the compound and an acid or alcohol (e.g., glycol monomethyl ether) in water may be heated, and then the mixture may be evaporated to dryness or the precipitated salt may be filtered by suction.

Additionally, the pharmaceutically acceptable metal salt may be prepared using a base. Alkali metal salts or alkaline earth metal salts are obtained, for example, by dissolving a compound in an excess amount of an alkali metal hydroxide solution or alkaline earth metal hydroxide solution and filtering off the non-dissolved compound salts, followed by evaporating and drying the filtrate.

The pharmaceutically acceptable salts of the compounds of the present disclosure, unless otherwise specified, may include salts of acidic or basic groups that may be present in the compounds of Formula 1 above and may be prepared using the conventional methods for preparing salts known in the art.

As used herein, the term "prevention" refers to all kinds of actions associated with the inhibition or delay of the occurrence, progression, and recurrence of non-alcoholic fatty liver disease (NAFLD) or dyslipidemia, by administering the pharmaceutical composition, and the term "treatment" refers to all kinds of actions associated with the improvement or advantageous changes in symptoms of NAFLD or dyslipidemia, by administering the above composition.

For example, the pharmaceutical composition according to the present disclosure may contain, as an active ingredient, the compounds represented by Formula 1 or a pharmaceutically acceptable salt thereof in an amount of 0.1 wt % to 75 wt % based on the total weight of the composition.

The NAFLD that can be prevented or treated by administering a pharmaceutical composition comprising the compounds of Formula 1 according to the present disclosure may be simple steatosis in the liver, steatohepatitis, or hepatocirrhosis, but the NAFLD is not limited thereto.

Additionally, the pharmaceutical composition comprising the compounds of Formula 1 according to the present disclosure may also be used for the prevention or treatment of dyslipidemia. For example, the pharmaceutical composition of the present disclosure may be used for the prevention or treatment of hyperlipidemia, hypercholesterolemia, or hypertriglyceridemia, but the diseases to be prevented or treated are not limited thereto.

Furthermore, the pharmaceutical composition comprising the compounds of Formula 1 according to the present disclosure may exhibit the effect of improving liver fibrosis.

Specifically, the pharmaceutical composition comprising the compounds of Formula 1 according to the present disclosure may reduce the expression of mRNAs associated with the liver diseases such as Serbp1, Col1a1, TIMP1, TNFα, etc.

In a specific embodiment of the present disclosure, in an NAFLD-induced mouse model, the compounds of Formula 1 according to the present disclosure not only showed the effects of reducing the steatosis scores and the mRNA expression levels associated with fat accumulation and liver fibrosis to normal levels, but also showed the effects of increasing the levels of high-density lipoprotein (HDL) in the blood while decreasing the levels of low-density lipoprotein (LDL). Accordingly, it was confirmed that the compounds of Formula 1 according to the present disclosure can directly ameliorate the symptoms of NAFLD, and in addition, can be used for the prevention and treatment of dyslipidemia such as hyperlipidemia, etc.

As used herein, the term "subject" refers to all kinds of animals including humans, monkeys, cattle, horses, sheep, pigs, chickens, turkeys, quails, cats, dogs, mice, rats, rabbits, and guinea pigs which have already developed or are at risk of developing NAFLD or dyslipidemia, and these diseases can be effectively prevented or treated by administering the pharmaceutical composition of the present disclosure to the subject. The pharmaceutical composition of the present disclosure may be administered in combination with existing therapeutic agents.

As used herein, the term "administration" refers to an introduction of a predetermined material into a patient by any suitable method. The composition of the present disclosure may be administered via any conventional route insofar as it can reach a target tissue. For example, the composition of the present disclosure may be administered via intraperitoneal, intravenous, intramuscular, subcutaneous, intradermal, oral, topical, intranasal, intrapulmonary, or intrarectal administration, but the administration route is not limited thereto. Additionally, the pharmaceutical composition of the present disclosure may be administered by any device capable of transferring an active material to the target cell.

The pharmaceutical composition according to the present disclosure may contain the compounds represented by Formula 1 or a pharmaceutically acceptable salt thereof as an active ingredient, and in addition, the composition may further contain a pharmaceutically acceptable carrier, diluent, or excipient. Furthermore, the composition may be formulated into various forms such as powders, granules, tablets, capsules, suspensions, emulsions, syrups, and aerosols for oral administration; sterile injection solutions for injections; etc. according to conventional methods to be suitable for each purpose of use.

The pharmaceutical composition according to the present disclosure is administered in a pharmaceutically effective amount or a therapeutically effective amount. As used herein, the term "pharmaceutically effective amount" refers to an amount sufficient for the treatment of diseases at a reasonable benefit/risk ratio applicable to medical treatment without causing any side effects, and the level of the effective dose may be determined based on the factors including health conditions of a patient, type of a disease, severity of illness, drug activity, drug sensitivity, administration method, administration time, administration route, dissolution rate, length of treatment, factors including drug(s) to be used simultaneously or in combination, and other factors well known in the medical field. It is important to administer the pharmaceutical composition in an amount to obtain the maximum effect with a minimum amount without adverse effects considering all of the factors described above, and the pharmaceutically effective amount can easily be determined by one of ordinary skill in the art.

Mode for Invention

Hereinafter, preferred examples are provided to help aid in the understanding of the present disclosure. However, the following examples are provided for a better understanding of the present disclosure, and the scope of the present disclosure is not limited by these Examples.

Various methods to synthesize starting materials for the synthesis of the compounds of the present disclosure are known, and these starting materials may be purchased from suppliers if they are commercially available. Examples of the reagent suppliers may include Sigma-Aldrich, TCI, Wako, Kanto, Fluorchem, Acros, Alfa, Fluka, Dae-Jung, etc., but the suppliers are not limited thereto. In addition, all of the commercially-available materials were used without further purification, unless otherwise provided.

Preparation Example 1: Preparation of Compounds Represented by Formula 1

[Formula 1]

The compounds represented by Formula 1 can be prepared according to the method disclosed in Korean Patent Application Publication No. 10-2016-0047378.

As a representative example, 2-(((3,3-dibutyl-5-(4-fluorophenyl)-7-methylthio-1,1-dioxido-2,3,4,5-tetrahydrobenzo[b][1,4]thiazepin-8-yl)methyl)amino)acetic acid (Compound 1) was prepared according to the method described in the above reference and used in Examples 1 to 3.

Example 1: Effects of Improving Blood Lipid Levels and Lowering Liver Fat in a Mouse Model with Non-Alcoholic Fatty Liver Disease (NAFLD) Induced by High-Fat High-Cholesterol Diet Eight-week-old C57BL/6J mice were supplied with a high-fat high-cholesterol diet (60% fat and 0.5% cholesterol) and drinking water containing 4.2% fructose for 16 weeks so as to induce non-alcoholic fatty liver disease (NAFLD). The mouse model is an experimental animal model that is known to exhibit pathological symptoms similar to those of fatty liver in humans.

After the supply of a high-fat high-cholesterol diet for 4 weeks, the diet was replaced with another high-fat high-cholesterol diet prepared to contain Compound 1 at a concentration of 0.016% and supplied for an additional 12 weeks, and the livers were removed by autopsy on the final day of the test. Parts of the removed livers were fixed in a 10% formalin solution for histopathology and tissue slides were prepared therefrom and subjected to H&E staining, whereas other parts of the removed livers were used for quantitative real-time PCR (qRT-PCR) analysis.

Figure 1:
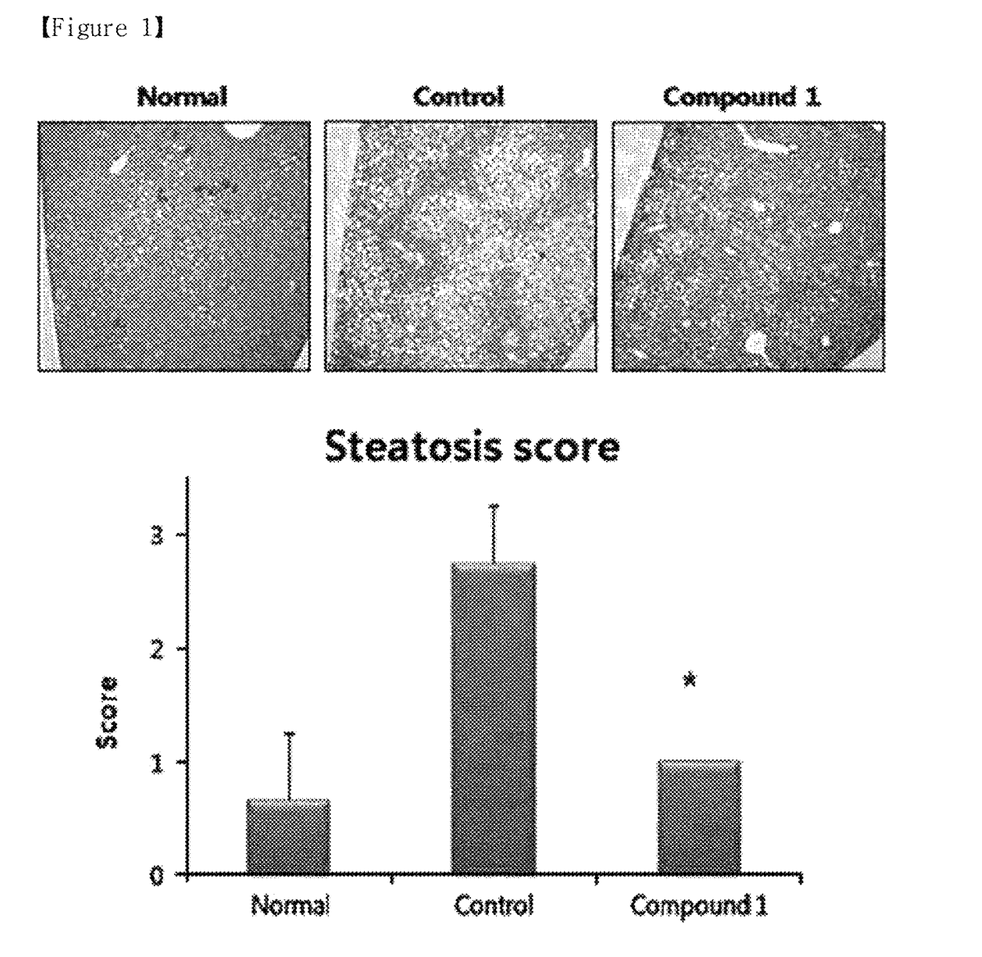
FIG. 1 shows H&E stained images of liver tissues obtained from NAFLD-induced mice and the steatosis scores obtained thereof, according to Example 1 of the present disclosure. Hereinafter, "Normal" represents a group of normal mice, "Control" represents a group of NAFLD-induced mice, and "Compound 1" represents an experimental group in which Compound 1 was provided in diet in inducing NAFLD.

The H&E-stained specimens were observed under a microscope for tissue readings and the results are shown in FIG. 1. The normal mice (not induced with NAFLD, denoted by "Normal" in drawings) and the mice induced with NAFLD using a high-fat high-cholesterol diet and fructose-containing drinking water (denoted by "Control" in drawings) were used as the control group. Specifically, histological scoring was performed in the same manner as in the clinical pathology scoring as follows: score 0 when the area occupied by fat in the liver tissue is less than 5%, score 1 when the area occupied by fat in the liver tissue is 5% to 33%, score 2 when the area occupied by fat in the liver tissue is 34% to 66%, and score 3 when the area occupied by fat in the liver tissue exceeds 66%. As shown in FIG. 1, the histological scoring showed that Control group, where NAFLD was induced with a high-fat high-cholesterol diet and fructose-containing drinking water, exhibited a significant increase in steatosis score compared to Normal group. Meanwhile, the experimental group (denoted by "Compound 1" in drawings), where a high-fat high-cholesterol diet containing 0.016% of Compound 1 according to the present disclosure was supplied, showed a significant decrease in steatosis score close to that of Normal group. These results indicate that Compound 1 has the effect of significantly reducing the symptoms of NAFLD.

Figure 2:
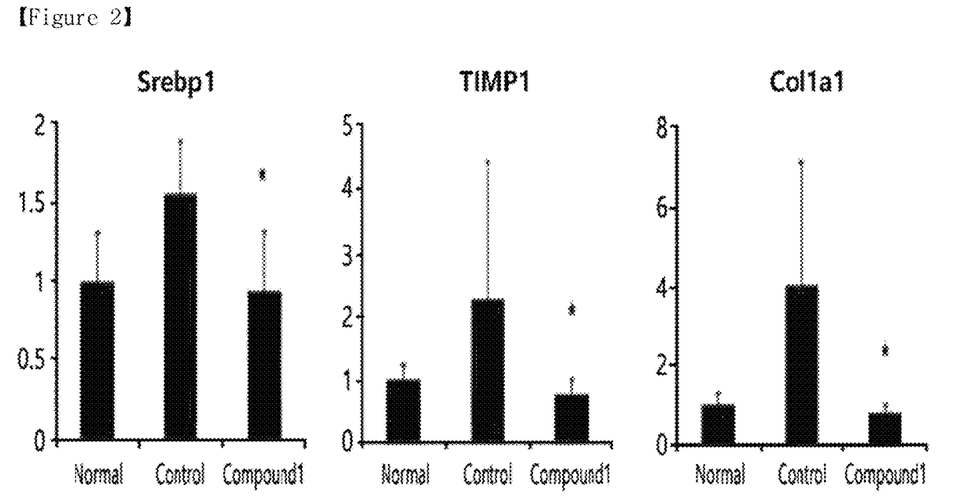
FIG. 2 shows the relative mRNA expression levels of the liver tissues obtained from NAFLD-induced mice, according to Example 1 of the present disclosure.

Furthermore, the relative expression level of mRNA in Normal group was calculated by qRT-PCR. Specifically, the mRNA expression levels of Srebp1 (i.e., a gene marker associated with lipid synthesis), and TIMP1 and Col1a1 (i.e., gene markers associated with fibrosis), etc. were measured through the SYBR-green RT-PCR analysis of the removed liver tissues described above, and the relative expression levels were calculated based on those of Normal group and are shown in FIG. 2. The calculated data were expressed in mean and standard deviation, and the significance of statistical differences between groups was confirmed using Student's t-test (*; $p<0.05$). As shown in FIG. 2, the NAFLD-induced Control group, showed a 1.6-fold, 2.3-fold, and 3.1-fold increase in the mRNA levels of Srebp1, TIMP1, and Col1a1, respectively, compared to those in Normal group. Meanwhile, the experimental group (Compound 1) showed a remarkable decrease with statistical significance in the mRNA levels of Srebp1, TIMP1, and Col1a1, which is a level similar to or less than those in Normal group. These results indicate that Compound 1 has the effects of ameliorating fibrosis as well as fat accumulation in the liver in an NAFLD-induced animal model.

Figure 3:
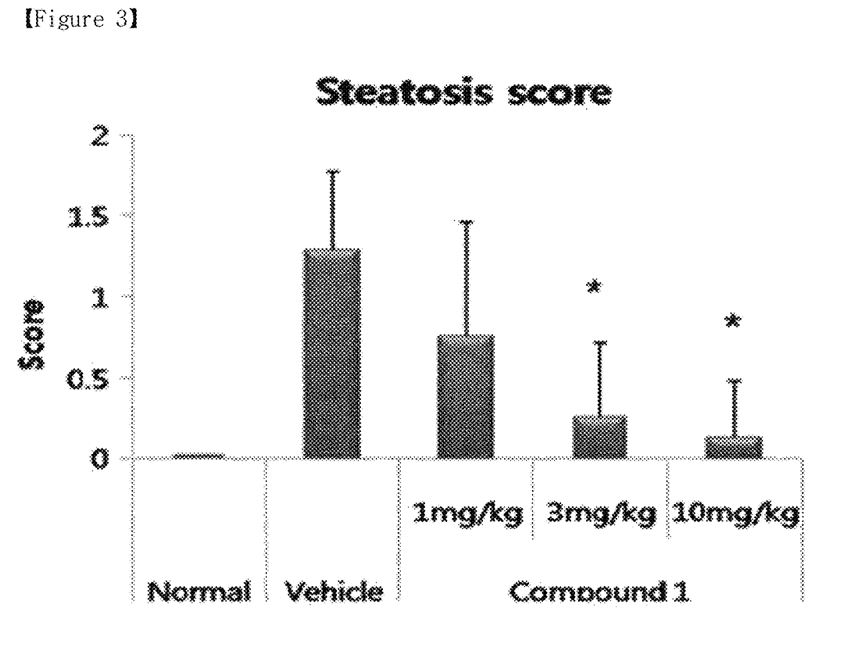
FIG. 3 shows the steatosis scores at varying doses of vehicle or Compound 1, according to Example 2 of the present disclosure.
Figure 4:
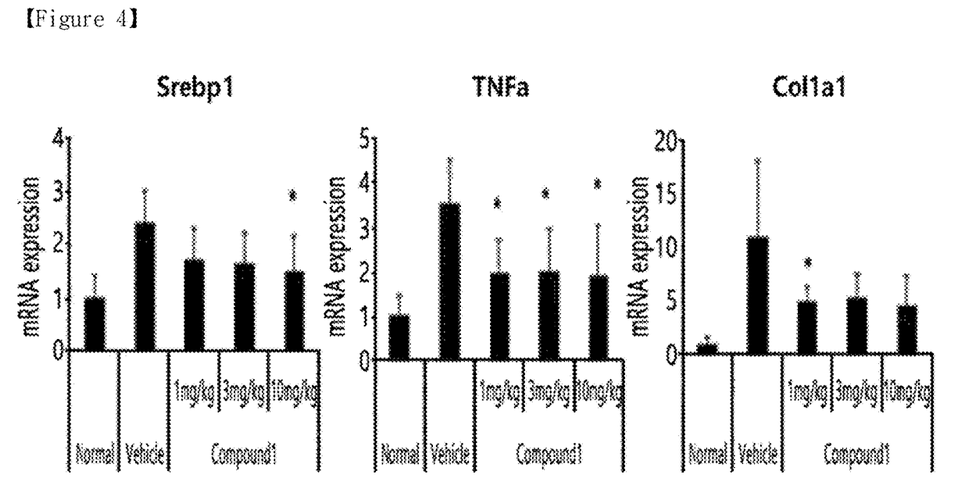
FIG. 4 shows the effect of varying doses of Compound 1 on the relative mRNA expression levels, according to Example 2 of the present disclosure.

Example 2: Effect of Inhibiting Gene Expression in a Mouse Model of NAFLD Induced by STZ Administration and High-Fat Diet Two-day-old C57BL/6J mice were administered with streptozotocin (STZ, 200 μg). Since the time the mice were 5 weeks old, they were supplied with a high-fat diet (60% fat) so as to induce NAFLD. The mouse model is an experimental animal model that is known to be capable of inducing diseases ranging from diabetes, fatty liver, steatohepatitis, liver fibrosis, to liver cancer within a short period of time of 20 weeks of age. Specifically, since the time the mice were 6 weeks old, they were orally administered with vehicle (0.5% hydroxypropyl methylcellulose+0.1% Tween 80) or Compound 1, which were prepared at various concentrations, at each concentration of 1 mg/kg, 3 mg/kg, and 10 mg/kg for 4 weeks, and the livers were removed by autopsy on the final day of the test. Parts of the removed livers were fixed in a 10% formalin solution for histopathology and tissue slides were prepared therefrom and subjected to H&E staining, whereas other parts of the removed livers were used for qRT-PCR analysis. The steatosis scores and relative mRNA expression levels were calculated in the same manner as in Example 1, and the results are shown in FIGS. 3 and 4, respectively. The calculated results were expressed in mean and standard deviation, and the significance of statistical differences between the groups was confirmed using Student's t-test (*; p<0.05).

As shown in FIG. 3, the experimental group, where Compound 1 was administered, showed lower steatosis scores compared to those in Control group, where vehicle (0.5% hydroxypropyl methylcellulose+0.1% Tween 80) was administered. The experimental group showed the effect of reduced steatosis score even at a dose of 1 mg/kg, and the effect was improved as dose increases, i.e, dose-dependently.

Additionally, as shown in FIG. 4, all in the experimental group in which the mice were administered with Compound 1 at 1 mg/kg, 3 mg/kg, and mg/kg showed significant decreases in the expression levels of the gene (mRNA) associated with lipid synthesis, inflammation, and fibrosis, compared to those of Control group.

Example 3: Effects of Reducing NAFLD Activity Score and Inhibiting Fibrosis in a Mouse Model of NAFLD Induced By STZ Administration And High-Fat Diet As in Example 2, vehicle or Compound 1 at a dose of 10 mg/kg was administered to the animal model in which NAFLD was induced by STZ administration and a high-fat diet. As a result, it was confirmed that the NAFLD activity score (NAS) of the vehicle-treated group was 4.8, indicating that NASH was induced. Additionally, two comparative groups were prepared by administering each of obeticholic acid (OCA, product name: Ocaliva) and compound A (having the same mechanism of action with Compound 1) at a dose of 10 mg/kg each, instead of vehicle or Compound 1. NAS values were respectively calculated for Normal group, the vehicle group, Compound 1 (10 mg/kg) group, and the two comparative groups (OCA-administered and compound A-administered groups), as shown in Table 2. NAS represents the sum of the scores for respective symptoms, i.e., steatosis, lobular inflammation, and hepatocyte ballooning, and the scoring for each symptom was based on the criteria described in Table 1 below. Each group consisted of 8 mice, and the NAS value is defined as the sum of the mean scores from each symptom. As NAS value is higher, NAFLD is more severe. For example, when NAS value is 3 to 4 points, the mouse can be suspected to have non-alcoholic steatohepatitis (NASH), whereas when NAS value is 5 points or higher, the mouse can be determined to have NASH.

TABLE 1

| Item | Score | Extent of Symptoms |
| --- | --- | --- |
| Steatosis | 0 | <5% |
|  | 1 | 5% to 33% |
|  | 2 | >33% to 66% |
|  | 3 | >66% |
| Lobular Inflammation | 0 | No Foci |
|  | 1 | <2 Foci/200× |
|  | 2 | 2 to 4 Foci/200× |
|  | 3 | >4 Foci/200× |
| Hepatocyte Ballooning | 0 | None |
|  | 1 | Some balloon cells |
|  | 2 | Many cells/Prominent ballooning |

TABLE 2

| Group | n | Steatosis | | | | Lobular Inflammation | | | | Hepatocyte Ballooning | | | NAS (Mean ± SD) |
| --- | --- | --- | --- | --- | --- | --- | --- | --- | --- | --- | --- | --- | --- |
|  |  | 0 | 1 | 2 | 3 | 0 | 1 | 2 | 3 | 0 | 1 | 2 |  |
| Normal | 8 | 8 | — | — | — | 8 | — | — | — | 8 | — | — | 0.0 ± 0.0 |
| Vehicle | 8 | — | 8 | — | — | — | — | 6 | 2 | — | 4 | 4 | ± |
| Comp. 1 | 8 | 4 | 4 | — | — | — | 2 | 5 | 1 | 6 | 1 | 1 | ± |
| Comp. A | 8 | 1 | 7 | — | — | — | — | 6 | 2 | 1 | 5 | 2 | ± |
| OCA | 8 | 2 | 6 | — | — | — | 1 | 5 | 2 | 4 | 4 | — | ± |

Figure 5:
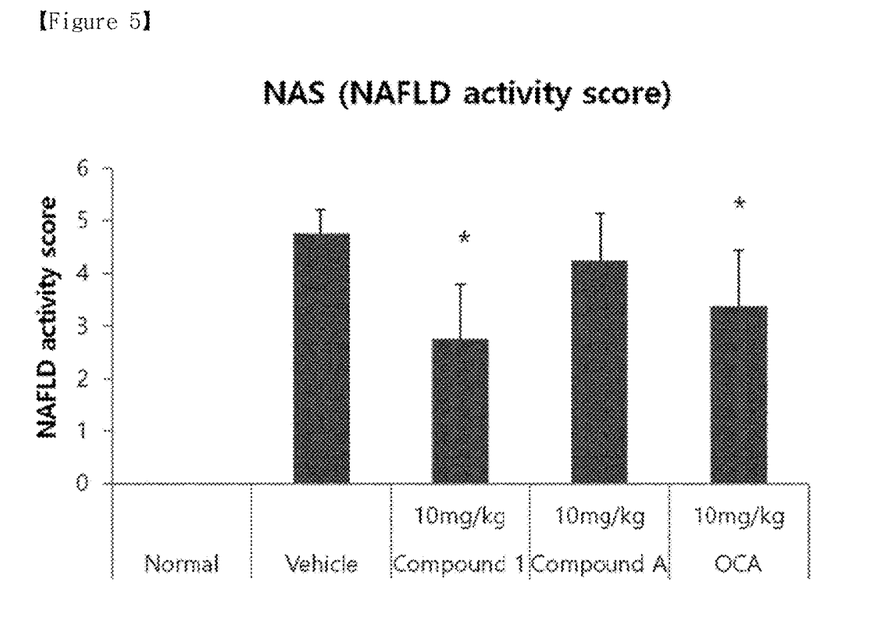
FIG. 5 shows the NAFLD activity scores (NAS) when administered with vehicle, Compound 1, Compound A, and obeticholic acid (OCA), according to Example 3 of the present disclosure.

The calculated NAS values are visualized in a bar graph for easy comparison and are shown in FIG. 5. The result for Compound 1 is a representative one which used the same dose as used in the comparative groups. As shown in FIG. 5, Compound 1 showed significantly reduced NAS values when compared to the comparative groups administered respectively with OCA and Compound A. These results indicate that Compound 1 of the present disclosure has a superior NASH inhibitory effect compared to OCA and Compound A, when administered at an identical dose.

Figure 6:
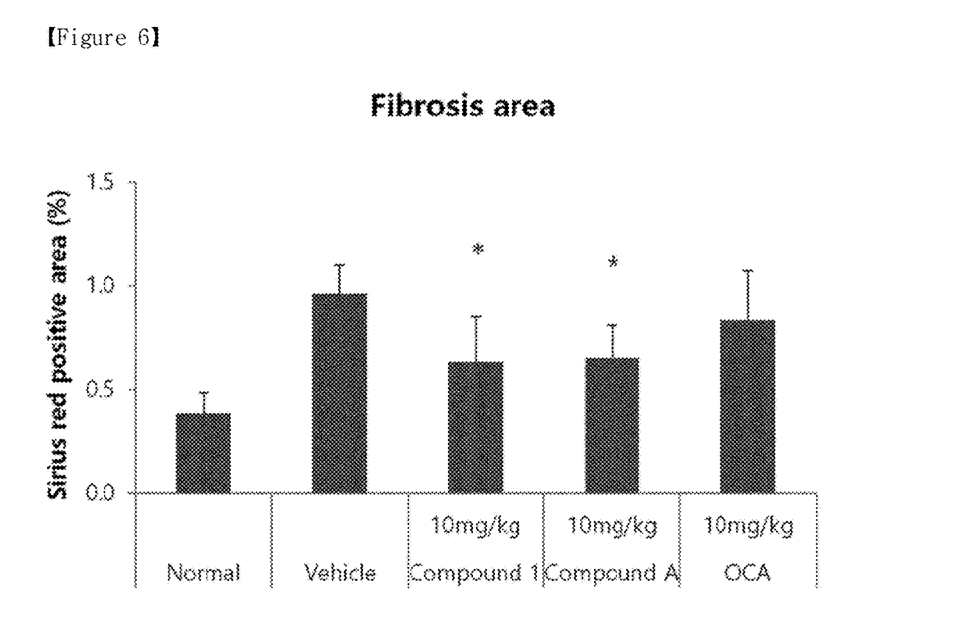
FIG. 6 shows the degree of fibrosis as identified by Sirius red staining when administered with vehicle, Compound 1, Compound A, and obeticholic acid (OCA), according to Example 3 of the present disclosure.

Furthermore, to determine the degree of fibrosis in liver tissues, the livers removed from each of the animal models were stained with Sirius Red, the stained areas (positive areas) were quantified by image analysis, and the results are shown in FIG. 6. As shown in FIG. 6, the experimental group administered with Compound 1 showed a significant decrease in the fibrosis area increased by NASH induction. In this experiment, it was confirmed that the degree of fibrosis in the Compound 1 group was similar to that in the comparative Compound A group, and Compound 1 group exhibited a superior fibrosis inhibitory effect compared to OCA group.

Example 4: Effect of Controlling Lipid Levels

Figure 7:
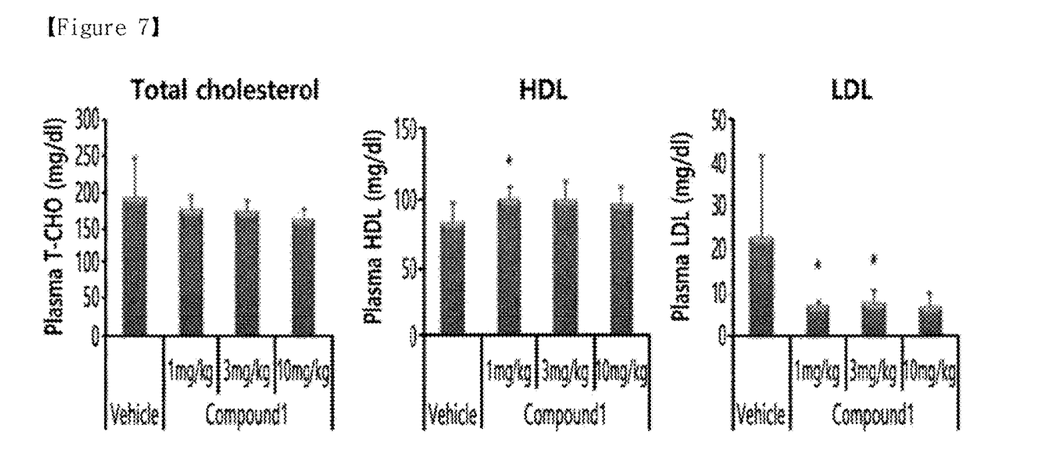
FIG. 7 shows the effect of vehicle or Compound 1 on the blood lipid content, at varying doses, according to Example 4 of the present disclosure.

Blood specimens were secured before autopsy by collecting blood samples from an experimental animal model prepared as in Example 2, in which NAFLD was induced by administering STZ and supplying a high-fat diet, and to which Compound 1 was administered at doses of 1 mg/kg, 3 mg/kg, and 10 mg/kg. The obtained blood samples were centrifuged to separate blood plasma, and the remaining samples were analyzed for blood lipid levels (e.g., levels of total cholesterol, high-density lipoprotein (HDL), and low-density lipoprotein (LDL)) using a biochemical analyzer (Hitachi 7100), and the results are shown in FIG. 7. The calculated results were expressed as mean and standard deviation, and the significance of statistical differences between the groups was confirmed using Student's t-test (*; p<0.05).

As shown in FIG. 7, the group where Compound 1 was administered showed a higher level of HDL and a lower level of LDL when compared to the vehicle administered group. These results indicate that Compound 1 can be used for the prevention or treatment of diseases such as hyperlipidemia or dyslipidemia accompanied by NAFLD.

The invention claimed is:

1. A method for treating non-alcoholic fatty liver disease (NAFLD) or dyslipidemia in a subject in need thereof, comprising administrating an effective amount of a pharmaceutical composition comprising a compound represented by Formula 1 below or a pharmaceutically acceptable salt thereof in the subject:

[Formula 1]

wherein
$R_1$ is hydroxy, carboxy, or hydroxysulfonyl($C_{1-4}$ alkyl);
$R_2$ and $R_3$ are each independently hydrogen, $C_{1-4}$ alkyl, hydroxy($C_{1-4}$ alkyl), carbamoyl($C_{1-4}$ alkyl), carboxy, carboxy($C_{1-4}$ alkyl), ($C_{5-10}$ heteroaryl)($C_{1-4}$ alkyl) or ($C_{5-10}$ aryl)($C_{1-4}$ alkyl), or $R_2$ and $R_3$, taken together with the respective carbon atom to which they are attached, form $C_{3-7}$ cycloalkyl;
$R_4$ is hydrogen or carboxy($C_{1-4}$ alkyl);
$R_5$ is hydrogen, halogen, ($C_{1-4}$ alkyl)thio, ($C_{1-4}$ alkyl) amino, or di($C_{1-4}$ alkyl)amino;
$R_6$ and $R_7$ are each independently $C_{1-6}$ alkyl;
$R_8$ and $R_9$ are each independently hydrogen, hydroxy, $C_{1-4}$ alkoxy, $C_{1-4}$ alkyl, halogen, nitro, cyano, amino, ($C_{1-4}$ alkyl)amino, di($C_{1-4}$ alkyl)amino, acetamido, formyl, $C_{1-4}$ alkanoyl, carboxy, carbamoyl, ($C_{1-4}$ alkyl) carbamoyl, di($C_{1-4}$ alkyl)carbamoyl, carbamoyloxy, ($C_{1-4}$ alkyl)carbamoyloxy, di($C_{1-4}$ alkyl)carbamoyloxy, ($C_{1-4}$ alkyl)sulfonyloxy, sulfamoyloxy, ($C_{1-4}$ alkyl)sulfamoyloxy, or di($C_{1-4}$ alkyl)sulfamoyloxy;
Q is $C_{5-19}$ aryl or $C_{5-19}$ heteroaryl; and
n is an integer of 0 to 3.

2. The method of claim 1,
wherein
$R_1$ is hydroxy, carboxy, or hydroxysulfonyl($C_{1-4}$ alkyl);
$R_2$ and $R_3$ are each independently hydrogen, $C_{1-4}$ alkyl, hydroxy($C_{1-4}$ alkyl), carbamoyl($C_{1-4}$ alkyl), carboxy, carboxy($C_{1-4}$ alkyl), or ($C_{5-10}$ heteroaryl)($C_{1-4}$ alkyl)), or $R_2$ and $R_3$, taken together with the respective carbon atom to which they are attached, form $C_{3-7}$ cycloalkyl;
$R_4$ is hydrogen or carboxy($C_{1-4}$ alkyl);
$R_5$ is ($C_{1-4}$ alkyl)thio, or di($C_{1-4}$ alkyl)amino;
$R_6$ and $R_7$ are each independently $C_{1-6}$ alkyl;
$R_8$ and $R_9$ are each independently hydrogen, hydroxy, halogen, or $C_{1-4}$ alkoxy;
Q is $C_{5-10}$ aryl; and
n is an integer of 0 to 3.

3. The method of claim 1, wherein $R_1$ is hydroxy, carboxy, or hydroxysulfonylmethyl.

4. The method of claim 1, wherein $R_2$ and $R_3$ are each independently hydrogen, carboxy, methyl, isobutyl, carbamoylmethyl, carboxymethyl, carboxyethyl, hydroxymethyl, imidazolylmethyl, indolylmethyl or ethyl, or $R_2$ and $R_3$, taken together with the respective carbon atom to which they are attached, form cyclopropyl.

5. The method of claim 1, wherein $R_4$ is hydrogen, carboxymethyl, or carboxyethyl.

6. The method of claim 1, wherein $R_5$ is methylthio, ethylthio, or dimethylamino.

7. The method of claim 1, wherein $R_6$ and $R_7$ are both butyl or ethyl.

8. The method of claim 1, wherein $R_8$ and $R_9$ are each independently hydrogen, hydroxy, methoxy, methyl, ethyl, fluoro, chloro, nitro, cyano, amino, methylamino, ethylamino, dimethylamino, acetyl, carboxy, carbamoyl, methylcarbamoyl, dimethylcarbamoyl, carbamoyloxy, methylcarbamoyloxy, dimethylcarbamoyloxy, methylsulfonyloxy, sulfamoyloxy, methylsulfamoyloxy, or dimethylsulfamoyloxy.

9. The method of claim 1, wherein Q is phenyl, pyridinyl, pyrimidinyl, or thiophenyl.

10. The method of claim 1, wherein the compound is selected from the group consisting of:
2-(((3,3-dibutyl-7-methylthio-1,1-dioxido-5-phenyl-2,3,4,5-tetrahydrobenzo[b][1,4]thiazepin-8-yl)methyl) amino)acetic acid;
3-(((3,3-dibutyl-7-methylthio-1,1-dioxido-5-phenyl-2,3,4,5-tetrahydrobenzo[b][1,4]thiazepin-8-yl)methyl) amino)propanoic acid;
2-(((3,3-dibutyl-7-methylthio-1,1-dioxido-5-phenyl-2,3,4,5-tetrahydrobenzo[b][1,4]thiazepin-8-yl)methyl) amino)succinic acid;
(S)-2-(((3,3-dibutyl-7-methylthio-1,1-dioxido-5-phenyl-2,3,4,5-tetrahydrobenzo[b][1,4]thiazepin-8-yl)methyl) amino)propanoic acid;
2-(((3,3-dibutyl-7-methylthio-1,1-dioxido-5-phenyl-2,3,4,5-tetrahydrobenzo[b][1,4]thiazepin-8-yl)methyl) amino)pentanedioic acid;
4-amino-2-(((3,3-dibutyl-7-methylthio-1,1-dioxido-5-phenyl-2,3,4,5-tetrahydrobenzo[b][1,4]thiazepin-8-yl) methyl)amino)-4-oxobutanoic acid;
(R)-2-(((3,3-dibutyl-7-methylthio-1,1-dioxido-5-phenyl-2,3,4,5-tetrahydrobenzo[b][1,4]thiazepin-8-yl)methyl) amino)propanoic acid;
2-(((3,3-dibutyl-7-methylthio-1,1-dioxido-5-phenyl-2,3,4,5-tetrahydrobenzo[b][1,4]thiazepin-8-yl)methyl) amino)-2-methylpropanoic acid;

(R)-2-(((3,3-dibutyl-7-methylthio-1,1-dioxido-5-phenyl-2,3,4,5-tetrahydrobenzo[b][1,4]thiazepin-8-yl)methyl)amino)-3-(1H-imidazol-4-yl)propanoic acid;
(R)-2-(((3,3-dibutyl-7-methylthio-1,1-dioxido-5-phenyl-2,3,4,5-tetrahydrobenzo[b][1,4]thiazepin-8-yl)methyl)amino)-3-(1H-indol-2-yl)propanoic acid;
(S)-2-(((3,3-dibutyl-7-methylthio-1,1-dioxido-5-phenyl-2,3,4,5-tetrahydrobenzo[b][1,4]thiazepin-8-yl)methyl)amino)-4-methylpentanoic acid;
(S)-2-(((3,3-dibutyl-7-methylthio-1,1-dioxido-5-phenyl-2,3,4,5-tetrahydrobenzo[b][1,4]thiazepin-8-yl)methyl)amino)pentanedioic acid;
(S)-2-(((3,3-dibutyl-7-methylthio-1,1-dioxido-5-phenyl-2,3,4,5-tetrahydrobenzo[b][1,4]thiazepin-8-yl)methyl)amino)-3-hydroxypropanoic acid;
3-((carboxymethyl)((3,3-dibutyl-7-methylthio-1,1-dioxido-5-phenyl-2,3,4,5-tetrahydrobenzo[b][1,4]thiazepin-8-yl)methyl)amino)propanoic acid;
3-(((3,3-dibutyl-7-methylthio-1,1-dioxido-5-phenyl-2,3,4,5-tetrahydrobenzo[b][1,4]thiazepin-8-yl)methyl)amino)pentanedioic acid;
2-(((3,3-dibutyl-7-methylthio-1,1-dioxido-5-phenyl-2,3,4,5-tetrahydrobenzo[b][1,4]thiazepin-8-yl)methyl)amino)-2-oxoacetic acid;
1-(((3,3-dibutyl-7-methylthio-1,1-dioxido-5-phenyl-2,3,4,5-tetrahydrobenzo[b][1,4]thiazepin-8-yl)methyl)amino)cyclopropanecarboxylic acid;
2-(((3,3-dibutyl-7-methylthio-1,1-dioxido-5-phenyl-2,3,4,5-tetrahydrobenzo[b][1,4]thiazepin-8-yl)methyl)amino)-2-oxoethanesulfonic acid;
2-(((3,3-dibutyl-5-(4-methoxyphenyl)-7-methylthio-1,1-dioxido-2,3,4,5-tetrahydrobenzo[b][1,4]thiazepin-8-yl)methyl)amino)acetic acid;
2-(((3,3-dibutyl-5-(4-hydroxyphenyl)-7-methylthio-1,1-dioxido-2,3,4,5-tetrahydrobenzo[b][1,4]thiazepin-8-yl)methyl)amino)acetic acid;
2-(((3,3-dibutyl-5-(3-methoxyphenyl)-7-methylthio-1,1-dioxido-2,3,4,5-tetrahydrobenzo[b][1,4]thiazepin-8-yl)methyl)amino)acetic acid;
2-(((3,3-dibutyl-5-(4-fluorophenyl)-7-methylthio-1,1-dioxido-2,3,4,5-tetrahydrobenzo[b][1,4]thiazepin-8-yl)methyl)amino)acetic acid;
2-(((3,3-dibutyl-5-(3-fluorophenyl)-7-methylthio-1,1-dioxido-2,3,4,5-tetrahydrobenzo[b][1,4]thiazepin-8-yl)methyl)amino)acetic acid;
2-(((3,3-dibutyl-5-(3-fluoro-4-methoxyphenyl)-7-methylthio-1,1-dioxido-2,3,4,5-tetrahydrobenzo[b][1,4]thiazepin-8-yl)methyl)amino)acetic acid;
2-(((3,3-dibutyl-5-(4-methoxyphenyl)-7-methylthio-1,1-dioxido-2,3,4,5-tetrahydrobenzo[b][1,4]thiazepin-8-yl)methyl)amino)-2-oxoethanesulfonic acid;
1-(((3,3-dibutyl-5-(3-fluoro-4-methoxyphenyl)-7-methylthio-1,1-dioxido-2,3,4,5-tetrahydrobenzo[b][1,4]thiazepin-8-yl)methyl)amino)cyclopropanecarboxylic acid;
2-(((3,3-dibutyl-5-(4-fluorophenyl)-7-methylthio-1,1-dioxido-2,3,4,5-tetrahydrobenzo[b][1,4]thiazepin-8-yl)methyl)amino)-2-oxoacetic acid;
(S)-2-(((3,3-dibutyl-5-(4-fluorophenyl)-7-methylthio-1,1-dioxido-2,3,4,5-tetrahydrobenzo[b][1,4]thiazepin-8-yl)methyl)amino)propanoic acid;
(S)-2-(((3,3-dibutyl-5-(4-fluorophenyl)-7-methylthio-1,1-dioxido-2,3,4,5-tetrahydrobenzo[b][1,4]thiazepin-8-yl)methyl)amino)-3-hydroxypropanoic acid; and
1-(((3,3-dibutyl-5-(4-fluorophenyl)-7-methylthio-1,1-dioxido-2,3,4,5-tetrahydrobenzo[b][1,4]thiazepin-8-yl)methyl)amino)cyclopropanecarboxylic acid.

11. The method of claim 1, wherein the non-alcoholic fatty liver disease comprises simple steatosis, steatohepatitis, or hepatocirrhosis.

12. The method of claim 1, wherein the dyslipidemia comprises hyperlipidemia, hypercholesterolemia, or hypertriglyceridemia.

13. The method of claim 1, wherein the pharmaceutical composition treats or ameliorates liver fibrosis.

14. The method of claim 1, wherein the compound is 2-(((3,3-dibutyl-5-(4-fluorophenyl)-7-methylthio-1,1-dioxido-2,3,4,5-tetrahydrobenzo[b][1,4]thiazepin-8-yl)methyl)amino)acetic acid.

15. The method of claim 1, wherein the pharmaceutical composition further contains a pharmaceutically acceptable carrier, diluent, or excipient.

16. The method of claim 1, wherein the compound represented by Formula 1 or the pharmaceutically acceptable salt thereof is contained in an amount of 0.1 wt% to 75 wt% based on the total weight of the composition.

17. A method for treating or ameliorating non-alcoholic fatty liver disease (NAFLD) in a subject in need thereof, comprising administrating an effective amount of 2-(((3,3-dibutyl-5-(4-fluorophenyl)-7-methylthio-1,1-dioxido-2,3,4,5-tetrahydrobenzo[b][1,4]thiazepin-8-yl)methyl)amino)acetic acid or a pharmaceutically acceptable salt thereof in the subject.

18. A method for treating or ameliorating dyslipidemia in a subject in need thereof, comprising administrating an effective amount of 2-(((3,3-dibutyl-5-(4-fluorophenyl)-7-methylthio-1,1-dioxido-2,3,4,5-tetrahydrobenzo[b][1,4]thiazepin-8-yl)methyl)amino)acetic acid or a pharmaceutically acceptable salt thereof in the subject.

* * * * *